US00PP25807P2

(12) United States Plant Patent
Dummen

(10) Patent No.: US PP25,807 P2
(45) Date of Patent: Aug. 11, 2015

(54) ***PORTULACA* PLANT NAMED 'DUECUPPY'**

(50) Latin Name: *Portulaca hybrida*
Varietal Denomination: Duecuppy

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 172 days.

(21) Appl. No.: 13/987,102

(22) Filed: Jul. 1, 2013

(51) Int. Cl.
*A01H 5/00* (2006.01)

(52) U.S. Cl.
USPC ..... Plt./471

(58) Field of Classification Search
USPC ..... Plt./471
See application file for complete search history.

*Primary Examiner* — Annette Para
(74) *Attorney, Agent, or Firm* — C. A. Whealy

(57) ABSTRACT

A new and distinct cultivar of *Portulaca* plant named 'Duecuppy', characterized by its semi-upright to spreading growth habit; vigorous growth habit; freely branching habit; freely flowering habit; and light red and yellow-colored flowers.

1 Drawing Sheet

Botanical designation: *Portulaca hybrida.*
Cultivar denomination: 'DUECUPPY'.

CROSS REFERENCED TO CLOSELY-RELATED APPLICATIONS

Title: *Portulaca* Plant Named 'DUECUPCAR'
Applicant: Tobias Dümmen
Filed: Concurrently with this application

BACKGROUND OF THE INVENTION

The present invention relates to a new and distinct cultivar of *Portulaca* plant, botanically known as *Portulaca hybrida* and hereinafter referred to by the name 'Duecuppy'.

The new *Portulaca* plant is a product of a planned breeding program conducted by the Inventor in Rheinberg, Germany. The objective of the breeding program is to create new semi-upright *Portulaca* plants with numerous attractive flowers.

The new *Portulaca* plant originated from a cross-pollination made by the Inventor in Rheinberg, Germany in July, 2010 of a proprietary selection of *Portulaca hybrida* identified as code number F-1921-019, not patented, as the female, or seed, parent with a proprietary selection of *Portulaca hybrida* identified as code number F-09-18, not patented, as the male, or pollen, parent. The new *Portulaca* plant was discovered and selected by the Inventor as a flowering plant from within the progeny of the stated cross-pollination in a controlled greenhouse environment in Rheinberg, Germany in May, 2012.

Asexual reproduction of the new *Portulaca* plant cuttings in a controlled greenhouse environment in Rheinberg, Germany since June, 2012, has shown that the unique features of this new *Portulaca* plant are stable and reproduced true to type in successive generations.

SUMMARY OF THE INVENTION

Plants of the new *Portulaca* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duecuppy'. These characteristics in combination distinguish 'Duecuppy' as a new and distinct *Portulaca* plant:

1. Semi-upright to spreading growth habit.
2. Vigorous growth habit.
3. Freely branching habit.
4. Freely flowering habit.
5. Light red and yellow-colored flowers.

Plants of the new *Portulaca* can be compared to plants of the female parent selection. Plants of the new *Portulaca* differ primarily from plants of the female parent selection in flower size as plants of the new *Portulaca* had larger flowers than plants of the female parent selection.

Plants of the new *Portulaca* can be compared to plants of the male parent selection. Plants of the new *Portulaca* differ primarily from plants of the male parent selection in flower color as plants of the male parent selection have red-colored flowers.

Plants of the new *Portulaca* can be compared to plants of *Portulaca hybrida* 'Duecupcar', disclosed in a U.S. Plant patent application Ser. No. 13/987,122. Plants of the new *Portulaca* and 'Duecupcar' differ primarily in flower color as plants of 'Duecupcar' have lighter-colored flowers.

Plants of the new *Portulaca* also can be compared to plants of the *Portulaca* 'Sun Dance Pink', not patented. In side-by-side comparisons conducted in Rheinberg, Germany, plants of the new *Portulaca* differed primarily from plants of 'Sun Dance Pink' in the following characteristics:

1. Plants of the new *Portulaca* were not as broad as plants of 'Sun Dance Pink'.
2. Plants of the new *Portulaca* were more freely branching than plants of 'Sun Dance Pink'.
3. Plants of the new *Portulaca* had darker green-colored leaves than plants of 'Sun Dance Pink'.
4. Plants of the new *Portulaca* and 'Sun Dance Pink' differed in flower color as plants of 'Sun Dance Pink' had bright pink-colored flowers.

5. Plants of the new *Portulaca* had shorter peduncles than plants of 'Sun Dance Pink'.

BRIEF DESCRIPTION OF THE PHOTOGRAPH

The accompanying colored photograph illustrates the overall appearance of the new *Portulaca* plant showing the colors as true as it is reasonably possible to obtain in colored reproductions of this type. Colors in the photograph may differ slightly from the color values cited in the detailed botanical description which accurately describe the colors of the new *Portulaca* plant.

The photograph comprises a side perspective view of a typical flowering plant of 'Duecuppy' grown in a container.

DETAILED BOTANICAL DESCRIPTION

The aforementioned photograph and following observations, measurements and values describe plants grown during the summer in 12-cm containers in a glass-covered greenhouse in Rheinberg, Germany and under cultural practices typical of commercial *Portulaca* production. During the production of the plants, day and night temperatures averaged 18° C. and light levels averaged 4,500 lux. Plants were pinched one time three weeks after planting and were 20 weeks old when the photograph and the description were taken. In the description, color references are made to The Royal Horticultural Society Colour Chart, 1995 Edition, except where general terms of ordinary dictionary significance are used.

Botanical classification: *Portulaca hybrida* 'Duecuppy'.

Parentage:

*Female, or seed, parent*.—Proprietary selection of *Portulaca hybrida* identified as code number F-1921-019, not patented.

*Male or pollen parent*.—Proprietary selection of *Portulaca hybrida* identified as code number F-09-18, not patented.

Propagation:

*Type*.—By cuttings.

*Time to initiate roots, summer*.—About five days at temperatures of 20° C.

*Time to initiate roots, winter*.—About seven days at temperatures of 20° C.

*Time to produce a rooted young plant, summer*.—About three weeks at temperatures of 20° C.

*Time to produce a rooted young plant, winter*.—About four weeks at temperatures of 20° C.

*Root description*.—Fine, fibrous; close to 159C in color.

*Rooting habit*.—Freely branching; dense.

Plant description:

*Plant and growth habit*.—Semi-upright to spreading plant habit; vigorous growth habit.

*Branching habit*.—Freely branching habit about 200 to 250 lateral branches potentially developing per plant; pinching enhances branching potential.

*Overall plant height*.—About 14 cm.

*Plant diameter* (*area of spread*).—About 45 cm.

Lateral branch description:

*Length*.—About 18.3 cm.

*Diameter*.—About 3.1 mm.

*Internode length*.—About 8.2 mm.

*Strength*.—Moderately strong.

*Texture*.—Smooth, glabrous.

*Color*.—Close to 144B and 199B.

Leaf description:

*Arrangement*.—Opposite, simple.

*Length*.—About 2.2 cm.

*Width*.—About 1 cm.

*Shape, developing leaves*.—Elliptic.

*Shape, fully expanded leaves*.—Obovate.

*Apex*.—Cuspidate.

*Base*.—Attenuate.

*Margin*.—Entire.

*Texture, upper and lower surfaces*.—Smooth, glabrous; fleshy, succulent.

*Venation pattern*.—Pinnate.

*Color*.—Developing and fully expanded leaves, upper surface: Close to 137B; venation, close to 150C. Developing and fully expanded leaves, lower surface: Close to 138B; venation, close to 150C.

*Petioles*.—Length: About 2 mm. Diameter: About 1.8 mm. Texture, upper and lower surfaces: Smooth, glabrous. Color, upper and lower surfaces: Close to 150C.

Flower description:

*Flower arrangement*.—Single rotate flowers; freely flowering habit with potentially about 500 to 1,750 flowers developing per plant; flowers face mostly upright.

*Fragrance*.—None detected.

*Natural flowering season*.—Plants begin flowering about twelve weeks after planting; in the garden, plants flower continuously from spring until autumn in Germany.

*Flower longevity*.—Flowers last about one day on the plant; flowers not persistent.

*Flower diameter*.—About 3.7 cm.

*Flower length* (*height*).—About 2 cm.

*Flower buds*.—Length: About 1 cm. Diameter: About 4.2 mm. Shape: Ovoid. Color: Close to 146C.

*Petals*.—Quantity per flower: Corolla consists of five petals fused at the base. Length: About 2 cm. Width: About 1.5 cm. Shape: Obovate. Apex: Emarginate. Margin: Entire. Texture, upper and lower surfaces: Smooth, glabrous. Color: When opening, upper surface: Close to 50A; center, close to 24A. When opening, lower surface: Close to 163B and 47B. Fully opened, upper surface: Close to 50A; center, close to 24A; color does not change with development. Fully opened, lower surface: Close to 163C and 47C.

*Sepals*.—Quantity per flower: Two or three fused into a tubular calyx. Length: About 6 mm. Width: About 4.8 mm. Shape: Ovate. Apex: Acuminate. Margin: Entire. Texture, upper and lower surfaces: Smooth, glabrous; leathery. Color, upper and lower surfaces: Close to 144B.

*Peduncles*.—Length: About 2.8 cm. Diameter: About 2.3 mm. Angle: Mostly upright. Strength: Moderately strong. Texture: Smooth, glabrous. Color: Close to 144A.

*Reproductive organs*.—Androecium: Quantity of stamens per flower: About 40 to 60. Filament length: About 2 mm to 4 mm. Filament color: Close to 9A. Anther shape: Oval, bi-lobed. Anther length: About 0.5 mm. Anther color: Close to 21B. Amount of pollen: Abundant. Pollen color: Close to 23A. Gynoecium: Pistil length: About 1.1 cm. Style length: About 5.8 mm. Style color: Close to 9A. Stigma color: Close to 9A. Ovary color: Close to 144D.

*Seeds & fruits*.—Seed and fruit production have not been observed on plants of the new *Portulaca*.

Garden performance: Plants of the new *Portulaca* have been observed to have good garden performance and to tolerate temperatures ranging from about 7° C. to about 40° C.

Pathogen & pest resistance: Plants of the new *Portulaca* have not been shown to be resistant to pathogens and pests common to *Portulaca* plants.

It is claimed:

1. A new and distinct *Portulaca* plant named 'Duecuppy' as illustrated and described.

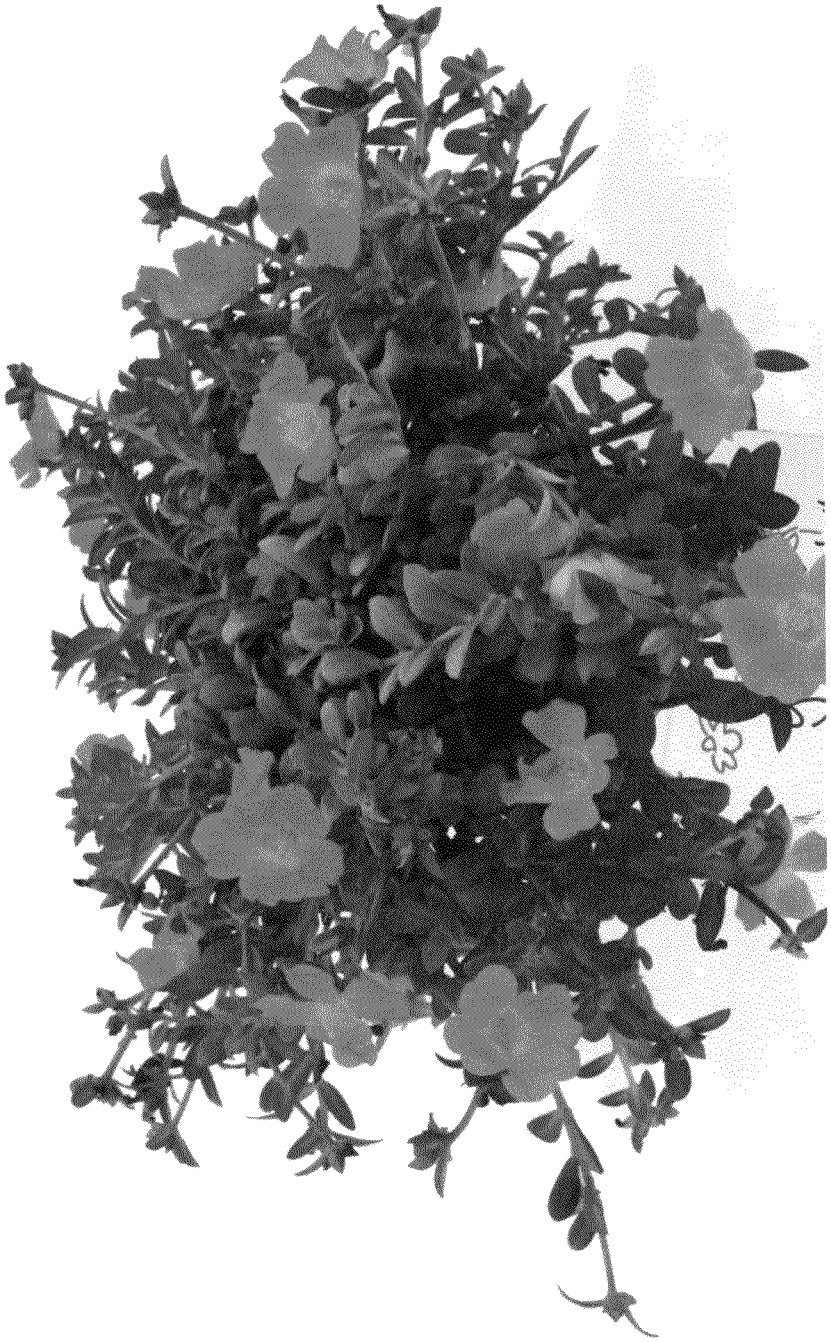

* * * * *